United States Patent [19]

Vogel et al.

[11] Patent Number: 4,599,905

[45] Date of Patent: Jul. 15, 1986

[54] METHOD AND APPARATUS FOR DETERMINING THE ELONGATION PROPERTY OF COPPER WIRE

[75] Inventors: Ralph A. Vogel, Three Rivers, Mich.; Keith E. Caudill, Fort Wayne, Ind.

[73] Assignee: Essex Group, Inc., Fort Wayne, Ind.

[21] Appl. No.: 760,231

[22] Filed: Jul. 29, 1985

[51] Int. Cl.$^4$ .............................................. G01N 3/08
[52] U.S. Cl. ...................................... 73/830; 73/826; 374/50
[58] Field of Search ................. 73/826, 828, 830, 834, 73/432 SD; 374/49, 50; 148/128

[56] References Cited

U.S. PATENT DOCUMENTS

| | | | |
|---|---|---|---|
| 2,436,317 | 2/1948 | Manjoine | 73/826 X |
| 3,100,253 | 8/1963 | O'Connor | 374/50 X |
| 3,453,863 | 7/1969 | Scott | 374/45 |

OTHER PUBLICATIONS

Heckel et al., Apparatus for Testing the Creep Behavior of Metallic Materials at Constant or Varying Temperatures and Constant Tensile Load, Materials Testing, Dec. 1968, vol. 10, #12, Dusseldorf.

*Primary Examiner*—Stephen A. Kreitman
*Assistant Examiner*—Scott M. Oldham
*Attorney, Agent, or Firm*—Robert D. Sommer

[57] ABSTRACT

A method and an apparatus for determining the eventual elongation property of a copper wire which has been cold drawn with an intermediate anneal and which is to be subsequently subjected to a predetermined heat treatment by a final in-line continuous anneal. Before a sample length of such wire is elongated to its breaking point in a tensile testing device, a capacitor is discharged through the wire length to produce a heating current flow therethrough of a magnitude and duration that produces a heat treatment of the wire length which approximately simulates that which would be the result of the final in-line continuous anneal. For this purpose, the wire holding devices of the tensile testing device have contact means to establish connection of the wire length in a discharge circuit for the capacitor.

6 Claims, 4 Drawing Figures

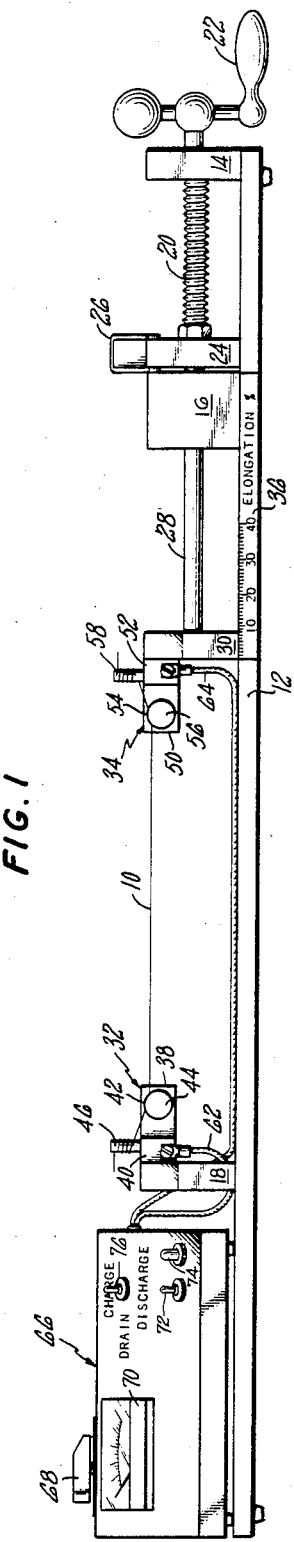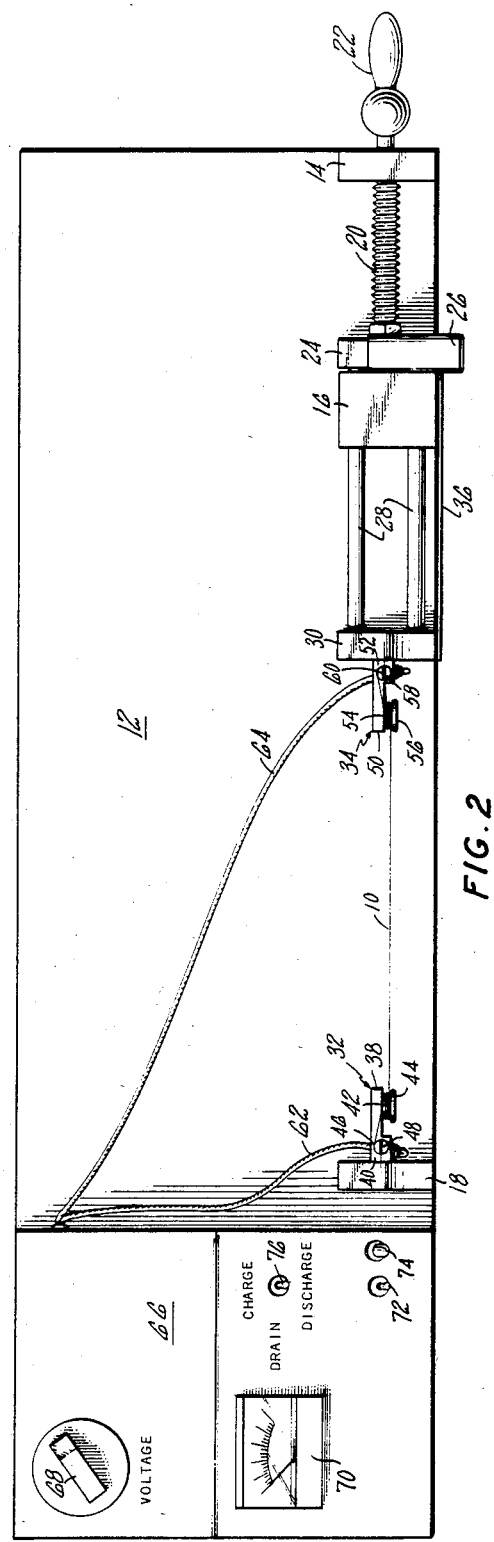

METHOD AND APPARATUS FOR DETERMINING THE ELONGATION PROPERTY OF COPPER WIRE

TECHNICAL FIELD

This invention relates to a method and an apparatus for determining the elongation property of copper wire and more particularly to an improved method and apparatus of the type in which a sample wire length is elongated to its breaking point.

BACKGROUND OF THE INVENTION

In the manufacture of insulated electric wire such as copper magnet wire, it is standard practice to test the wire to determine whether the elongation property of the wire meets manufacturing specifications. This is accomplished by clamping a sample length of wire in two holding devices spaced a predetermined distance apart, and then moving one of the holding devices relative to the other until the wire breaks. The elongation property of the wire is indicated by the distance traveled by the movable holding device relative to the fixed holding device.

The final mechanical properties of copper wire are significantly affected by its overall processing history. In a wire manufacturing process disclosed in our co-pending application Ser. No. 671,275, filed Nov. 13, 1984, copper wire of improved mechanical properties is obtained by cold drawing wire through a first series of dies to form an intermediate diameter wire, suitably annealing the intermediate diameter wire, and then cold drawing the intermediate diameter wire through a second series of dies to form a wire of a final desired diameter. This wire drawing process with an intermediate anneal produces copper wire which has the ability to be subsequently quickly annealed at relatively low temperatures in a final annealing step to give an end product of superior mechanical properties. This final annealing step is advantageously performed as an in-line continuous anneal in connection with an enamel applying and curing operation. However, the end product may have unacceptable mechanical properties if the intermediate anneal was incompletely or not performed. As a result, substantial quantities of finished wire products may be wasted.

Accordingly, it would be desirable to determine the eventual elongation property of a copper wire which has been cold drawn with an intermediate anneal by testing of the wire before it is subjected to the final in-line continuous anneal and coating operations. Determining the elongation property of copper wire at this intermediate stage of manufacture by known methods, however, is of no avail since there is no discernible difference between the elongation values of wire cold drawn with or without an intermediate anneal.

SUMMARY OF THE INVENTION

The present invention provides a method and an apparatus for determining the eventual elongation property of a copper wire which has been cold drawn with an intermediate anneal and which is to be subsequently subjected to a predetermined heat treatment by a final in-line continuous anneal. In accordance with this invention, a representative length of the copper wire is secured at longitudinally spaced points thereof and an electric voltage is applied to the wire length at the spaced points for a period of short duration to cause a heating current flow through the wire length which effects a heat treatment of the wire length that approximately simulates that which would be the result of the final in-line continuous anneal. The wire length is then elongated to its breaking point and the amount of elongation of the wire length at the instant of breaking is measured. The voltage applied is suitably a pulse of electrical energy obtained by discharge of a capacitor through the wire length.

In a preferred embodiment of the invention, an apparatus for elongating a length of copper wire to its breaking point includes two wire holding means, one of which is movable relative to the other. Contact means on the wire holding means establish electrical connections to longitudinally spaced points of the wire length. An electric power supply means is provided to apply an electric voltage of selected characteristics to the contact means for producing a heating current flow through the wire length which effects a predetermined heat treatment of the wire length. The power supply means suitably includes a capacitor, a charging circuit for charging the capacitor to a desired potential, and switch means for alternately connecting the capacitor to the charging circuit and to the contact means for discharge of the capacitor through the wire length.

For a better understanding of the invention, reference may be had to the following detailed description taken in connection with the accompanying drawing, in which:

BRIEF DESCRIPTION OF THE DRAWINGS

FIG. 1 is a front elevational view of an apparatus for determining the elongation property of wire, illustrating the method and apparatus of the present invention:

FIG. 2 is a top plan view of the apparatus of FIG. 1;

BEST MODE FOR CARRYING OUT THE INVENTION

Figure 3:
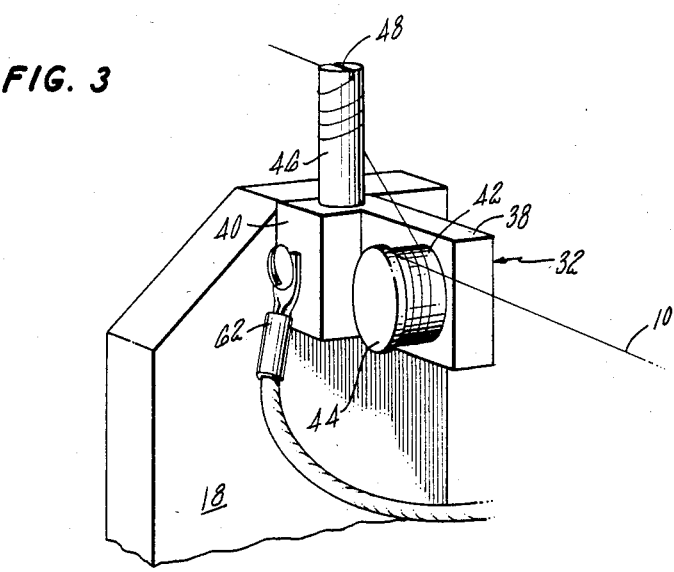
FIG. 3 is an enlarged perspective view of one of the wire holding devices employed in the apparatus of FIG. 1.

Referring first to FIGS. 1, 2 and 3 of the drawings, there is shown apparatus for determining the elongation property of a wire 10. This apparatus includes a base plate or support 12, upon the upper surface of which are mounted three spaced blocks 14, 16 and 18. A screw 20 having a crank 22 attached to one end thereof is rotatably mounted in the blocks 14 and 16 and is held against longitudinal movement relative to these blocks. The other end of the screw 20 is threaded through a movable crosshead 24 which is movable toward and from the block 14 upon rotation of the screw 20 by the crank 22. The crosshead 24 may be provided with a clutch (not shows) that is operable by a lever 26 to disengage the crosshead 24 from the screw 20 for free longitudinal movement of the crosshead 24 independently of the screw 20. Two guide rods 28 extend from the crosshead 24 through guide openings in the block 16 and are conected at their other ends by a crosshead 30. The block 18 and the crosshead 30 support holding devices 32 and 34, respectively, for securing the wire length 10 in a position for determining its elongation property. A graduated scale 36 is affixed to a vertical edge of the base place 12 for measuring the movement of the crosshead 30.

Apparatus of the character thus far described is well-known in the wire industry and is commonly used to determine the elongation property of wire. After a wire length 10 has been secured to the holding devices 32 and 34 in a taut condition, the screw 20 is rotated with the crank 22 so as to move the crosshead 30 in a direction away from the block 18 and subject the wire length 10 to an increasing tensile force. Continued rotation of the screw causes elongation of the wire length 10 to its breaking point. The amount of elongation of the wire length 10 at the instant of breaking can be determined by measuring the distance the crosshead 30 moved along the scale 36.

This type of apparatus can accurately determine the elongation property of copper wire possessed by it at any of the various stages of a wire manufacturing process. In the past, however, testing of copper wire with this type of apparatus at an intermediate stage of the wire manufacturing process would not necessarily provide an indication of the eventual elongation value which the wire would possess after being subjected to a subsequent annealing. Copper wire which has been cold drawn with a proper intermediate anneal in the wire drawing sequence may have substantially the same elongation value as that of a copper wire which has been cold drawn without such an intermediate anneal. Thus a comparison of the elongation values of such wires after being drawn would not reveal that the wire drawn with an intermediate anneal is more readily annealed during a subsequent annealing and will have an eventual elongation value substantially higher after a subsequent anneal than that of the wire drawn without an intermediate anneal. To determine whether a copper wire was drawn with a proper intermediate anneal, it therefore has been necessary to complete the wire manufacturing process and measure the eventual elongation value of the wire after a final anneal.

The improved apparatus of the present invention permits the eventual elongation property of a cold drawn wire to be accurately determined without completing the wire manufacturing process on a production line. As shown in FIGS. 1, 2 and 3, the wire holding device 32 includes a horizontally extending bar 38 with an enlarged end 40 suitably secured to the block 18 in spaced relation with base plate 12. A stud 42 is suitably secured at one side of the bar 38 and has a head 44. A vertical pin 46 suitably secured in the end 40 of the bar 38 is provided with a slot 48 in its upper end. The wire holding device 34 is similar to the holding device 32 and includes a horizontally extending bar 50 with an enlarged end 52 suitably secured to the crosshead 30. A stud 54 with a head 56 and a vertical pin 58 with a slot 60 in its upper end are carried by the bar 50.

The bars 38 and 50 together with studs 42 and 54 are formed of an electrically conductive material such as aluminum or brass so that electrical connections may be made with the ends of the wire 10 when wrapped about the studs 42 and 54. An insulated electric conductor 62 is suitably secured at one end to the bar 38 and another insulated electric conductor 64 is suitably secured at one end to the bar 50. The conductors 62 and 64 have their other ends connected to an electric power supply apparatus 66. The block 18 and the crosshead 30 are each preferably formed from a suitable rigid insulation material.

The power supply apparatus 66 has a control knob 68 for adjusting the output voltage level of the apparatus 66 and a voltmeter 70 to indicate the adjusted value.

Figure 4:
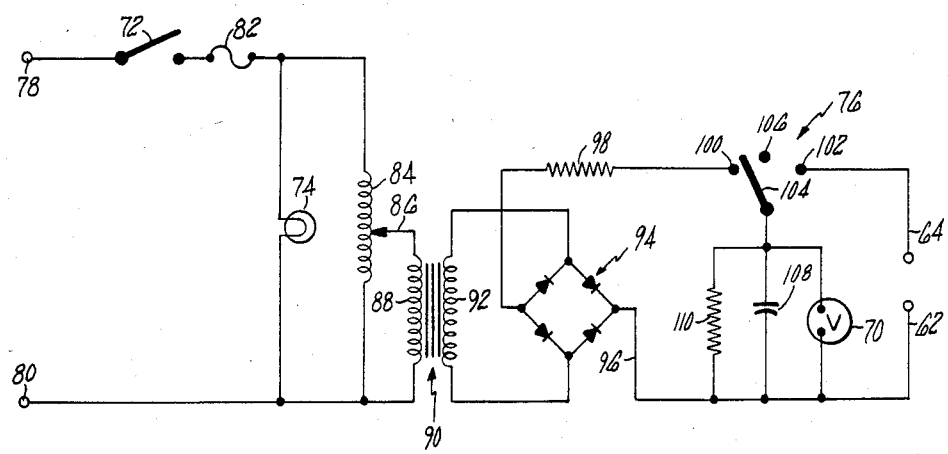
FIG. 4 is a schematic wiring diagram of the power supply apparatus employed in the apparatus of FIG. 1.

The apparatus 66 also includes an on/off switch 72, a pilot light 74, and a selector switch 76. As shown by the circuit diagram of FIG. 4, the apparatus 66 is energized from a suitable source of A.C. electrical power supplied through input terminals 78 and 80, the on/off switch 72, and a fuse 82 to the pilot light 74 and to opposite sides of an adjustable auto-transformer 84. The auto-transformer 84 has a sliding contact 86 operated by the control knob 68 to adjust the A.C. voltage supplied to the primary winding 88 of a step-down transformer 90. The secondary winding 92 of the transformer 90 is connected to the input terminals of a bridge rectifier 94 which has one output terminal connected to a lead 96 and another output terminal connected through a current limiting resistor 98 to one stationary contact 100 of the selector switch 76. The conductor 62 is connected to the lead 96 and the conductor 64 is connected to another stationary contact 102 of the selector switch 76. The movable contact 104 of the switch 76 is movable between the contacts 100 and 102 and is also movable to an intermediate position indicated by a stationary contact 106. A capacitor 108 connected between the lead 96 and the movable contact 104 is in parallel connection with the voltmeter 70 and a drain resistor 110.

It will be noted that when switch 76 is operated to engage movable contact 104 with stationary contact 100 there is established a charging circuit for charging the capacitor 108 to a desired direct current potential determined by the position of sliding contact 86 on the auto-transformer 84. Upon subsequent transfer of the movable contact 104 to the stationary contact 102 there is completed a discharge circuit for discharge of the capacitor 108 through a wire length 10 that is secured to the holding devices 32 and 34. By operating the switch 76 to the intermediate position of the movable contact 104, any charge on the capacitor 108 may be dissipated by discharge through the resistor 110.

By placing a suitable charge upon the capacitor 108 and then discharging the capacitor 108 through a wire length 10, an electric voltage of short duration is applied to the wire length 10 to cause a heating current flow through the wire length. The magnitude and duration of this heating current can be selected for various wire sizes to effect a Predetermined heat treatment of the wire length that approximately simulates that heat treatment which would be the result of a final anneal in the wire manufacturing process. For ten-inch lengths of copper wire in the size range of AWG32 to AWG44, appropriate heating current flows are obtained with a 70,000 microfarad capacitor 108 charged to voltages ranging from 21 volts for the larger wire sizes to about 9 volts for the smaller wire sizes. The heat treatment of copper wire effected by such heating current flows approximately simulates that which is the result of a continuous in-line anneal at a temperature of about 700° F. for a time of about one second.

In carrying out the method of the present invention, the crosshead 30 is moved to its extended position at the "O" end of the graduated scale 36. A length of wire 10 is secured in taut condition between the contact studs 42 and 54 by wrapping opposite ends of the wire about the respective studs and tightly winding several wire turns around each of the respective pins 46 and 58 before inserting the free ends of the wire into the respective slots 48 and 60. With the switch 72 of the apparatus in its "on" position and the selector switch 76 in its "charge" position, the control knob 68 is operated to set the charging voltage for the capacitor 108 to the appropriate value as indicated by the voltmeter 70. After charging of the capacitor 108 to the selected voltage, the selector switch 76 is actuated to its "discharge" position to apply the capacitor voltage to the wire length 10 at the two spaced points thereof in engagement with the respective studs 42 and 54. The capacitor 108 rapidly discharges through the wire length 10 causing a pulse of electrical energy to be applied across the wire length which is of sufficient magnitude and duration to cause the desired heating current flow through the wire length.

Thereafter, the screw 20 is slowly rotated with the crank 22 to move the crosshead 30 in a direction away from the block 18, thus subjecting the wire length 10 to an increasing tensile force. The crank 22 is turned to increase the distance between the block 18 and the crosshead 30 until the wire length 10 is elongated to its breaking point. Reference to the graduations marked on the scale 36 indicates the amount of elongation of the wire length at the instant of breaking.

From the foregoing, it will be evident that the elongation testing method and apparatus of the present invention permits the eventual elongation property of a cold drawn wire to be accurately determined without completing the wire manufacturing process on a production line. Thus an effective monitoring and control of intermediate annealing in wire drawing operations can be achieved with significant savings in production time and scrap costs.

What is claimed is:

1. The method of determining the eventual elongation property of a copper wire which has been cold drawn with an intermediate anneal and which is to be subsequently subjected to a final in-line continuous anneal at a selected elevated temperature for a selected time interval comprising the following steps in sequence:

obtaining a representative length of said copper wire which has been cold drawn with an intermediate anneal but which has not been subjected to a further final anneal;

securing said wire length in taut condition at two longitudinally spaced points thereof by mounting said wire length at its ends to respective first and second wire holding means which are movable relative one to another;

while maintaining said wire length mounted in taut condition to said wire holding means, applying an electric voltage for a period of short duration at said two spaced points to cause a heating current flow through said wire length between said two spaced points, the magnitude and the duration of such heating current flow being such as to effect a predetermined heat treatment of said wire length which approximately simulates that which would be the result of said final in-line continuous anneal;

thereafter moving one of said wire holding means relative to the other and thereby subjecting said wire length to an increasing tensile force between said two spaced points to elongate said wire length unitl it breaks, and measuring the amount of the elongation of said wire length at the instant of breaking to ascertain the eventual elongation property of said copper wire which would be attained after said final in-line continuous anneal.

2. The method of claim 1 wherein the step of applying an electric voltage at said two spaced points is carried out by sending an electrical capacitor discharge through said wire length between said two spaced points to cause said heating current flow through said wire length.

3. The method of claim 1 wherein the step of applying an electric voltage at said two spaced points is carried out by charging a capacitor of selected capacitance value to a predetermined potential from a suitable source of direct current potential and then connecting said charged capacitor across said wire length at said two spaced points to cause said heating current flow through said wire length.

4. In apparatus for elongating a sample of copper wire to its breaking point for determining the elongation property of the wire which includes first and second wire holding means for securing a length of wire at two longitudinally spaced points thereon, means for moving one of said holding means relative to the other to subject said wire length to an increasing tensile force between said two spaced points and to elongate said wire length until it breaks, and means for measuring the amount of the elongation of said wire length at the instant of breaking; the improvement comprising: contact means on said holding means to engage said wire length and to establish electrical connections thereto at said two spaced points; and electric power supply means connected to said contact means for sending an electrical capacitor discharge through said wire length to cause a heating current flow of brief duration through said wire length when secured to said holding means but prior to being subjected to elongation thereof between said holding means; said power supply means including means to supply said electrical capacitor discharge with selected characteristics which produces a heating current flow through said wire length of a magnitude and duration such as to effect a predetermined heat treatment of said wire length which approximately simulates that which would be the result of an in-line continuous anneal of said wire length at a selected elevated temperature for a selected time interval.

5. The invention of claim 4 wherein said power supply means include a capacitor of selected capacitance value, a charging circuit for charging said capacitor to a desired potential, and switch means for alternately connecting said capacitor to said charging circuit and to said contact means on said holding means for discharge of said capacitor when charged through said wire length.

6. The invention of claim 5 wherein said charging circuit includes means to apply to said capacitor a direct current potential that is selectively variable over a range of desired potentials.

* * * * *